United States Patent [19]

Kamath et al.

[11] Patent Number: 5,261,267

[45] Date of Patent: Nov. 16, 1993

[54] METHOD AND APPARATUS FOR ROCK PROPERTY DETERMINATION USING PRESSURE TRANSIENT TECHNIQUES AND VARIABLE VOLUME VESSELS

[75] Inventors: Jairam Kamath, Redondo Beach; Russ E. Boyer; Frank M. Nakagawa, both of Fullerton, all of Calif.

[73] Assignee: Chevron Research and Technology Company, San Francisco, Calif.

[21] Appl. No.: 763,082

[22] Filed: Sep. 20, 1991

[51] Int. Cl.$^5$ ............................................. G01N 15/08
[52] U.S. Cl. ............................................. 73/38
[58] Field of Search ............................. 73/153, 38, 37

[56] References Cited

U.S. PATENT DOCUMENTS

| | | | |
|---|---|---|---|
| 2,867,116 | 1/1959 | Aronofsky et al. | 73/38 |
| 4,537,063 | 8/1985 | Barnaby | 73/38 |
| 4,555,934 | 12/1985 | Freeman et al. | 73/38 |
| 4,627,270 | 12/1986 | Jones | 73/38 |

OTHER PUBLICATIONS

*A Transient Laboratory Method for Determining the Hydraulic Properties of "Tight" Rocks—I. Theory,* P. A. Hsieh et al, Int. J. Rock Mech. Min Sci. & Geomech. Abstr., vol. 18, pp. 245–252 (1981).

*Primary Examiner*—Hezron E. William
*Assistant Examiner*—Michael Brock
*Attorney, Agent, or Firm*—Edward J. Keeling; Matt W. Carson

[57] ABSTRACT

Method and apparatus for determining heterogeneous properties of a core sample by use of pressure transients. In the method, a pressure is applied to a first closed vessel at one end of a core sample. The pressure is then allowed to dissipate into the core and into a second closed vessel at the other end of the core sample. The pressure in at least one of the vessels or the core itself is measured and recorded as a function of time during the pressure dissipation. The volume of the first vessel is then varied and pressure is once again applied to the first vessel and allowed to dissipate into the core and second vessel. The pressure is again measured and recorded as a function of time during the pressure dissipation. The two sets of recorded measurements are then analyzed to detect deviations from theoretical responses in homogeneous cores which identify heterogeneities. Preferably, the volume of the first vessel has in either the first or second test a volume sufficiently small to cause a measurable variance between an actual pressure transient response for the system and a theoretical pressure transient response for the system. By using a small volume in both tests and reversing the direction of the second test, different heterogeneous properties may be detected.

24 Claims, 8 Drawing Sheets

FIG_1

FIG_2

FIG_3

FIG_5

FIG_4a

FIG_4b

FIG_6

FIG_8

FIG_7

FIG_9

FIG_10

FIG_11

METHOD AND APPARATUS FOR ROCK PROPERTY DETERMINATION USING PRESSURE TRANSIENT TECHNIQUES AND VARIABLE VOLUME VESSELS

BACKGROUND OF THE INVENTION

This invention relates to a method and apparatus for determining properties of core samples and, more particularly, to such a method and apparatus where various properties of a geological core sample are determined using pressure transient techniques and variable volume reservoir vessels. Another name for pressure transients is "pressure decay". These two terms will be used interchangeably throughout the description of the invention.

The properties measured from a subterranean rock core sample are important in evaluating the extent and production potential of petroleum and other valuable mineral deposits which may be present in a geologic formation. Property determination of samples from formations currently under production, as well as from formations not yet under production, are of importance.

The detection of heterogeneities within rock samples, the location of fluid fronts or damaged zones, determination of permeabilities of different zones using a single test, and measurement of core porosity or pore volume compressibility are variables of importance in geologic evaluation. In recent years, the exploration and production of petroleum from formations of complex structure has greatly increased. Consequently, the need to measure the properties of many core samples has also accelerated.

While various means of testing core samples to determine bulk permeability exist, the determination of varying properties has been generally through estimation techniques, for example the use of time intensive tracer tests. Bulk permeability is a permeability measurement that assumes the core is homogeneous, and ignores heterogeneities. Permeability measurement using pressure transient techniques, assuming homogeneous cores, was originated by W. F. Brace et al in "Permeability of Granite Under High Pressure," Journal of Geophysical Research (1968), Vol. 73, p. 2225–2236. The technique of Brace has been used by those interested in radioactive waste storage, tight gas sand reservoirs, heavy oil recovery, and low permeability oil field rocks, such as shales. However, the technique of Brace neglected the compressive storage of the rock sample in the development of the analytical equations describing the measurement process. The error in the determination of permeability due to this assumption was minimized by the use of large reservoir vessels in the test apparatus, such that their compressive storage far exceeded the storage of the rock sample.

Others have developed measurement techniques for permeability of core samples, but all prior theoretical analyses assume a homogeneous structure. As stated earlier, physical methods which are capable of quantitatively discerning heterogeneities, such as tracers, are complicated and expensive flow tests to conduct. As a result of such short-comings of prior methods, the method and apparatus disclosed herein were developed. In accordance with the present invention, measurement of multiple properties of a core sample may be made using a single test apparatus and with greater rapidity than previously possible.

SUMMARY OF THE INVENTION

A method and apparatus for determining core sample heterogeneities by use of pressure transient testing is disclosed. The invention makes use of the discovery that when pressure transient tests are run using testing vessels whose compressive storages are about equal to the compressive storage of the core, heterogeneities in the core will cause the pressure transient response to deviate from the theoretical response. The theoretical response is the response that would result for a homogeneous core. Thus, by analyzing the deviation of the pressure transient responses from the theoretical response, heterogeneities can be identified, qualified, and in some cases quantified. To generate enough data to highlight the deviations from theoretical, and to accommodate the range of core samples having different compressive storage values which might be encountered, an apparatus was designed which incorporates a variable small volume vessel. In the preferred mode, vessels having a large compressive storage with respect to the core compressive storage are included in the apparatus so that data from pressure transient tests using these larger vessels can be analyzed alongside data from pressure transients using the small vessels.

In one embodiment, pressure transient tests using small pressure transient vessels are run in opposite directions on a core sample. The results are then analyzed to locate a longitudinal core permeability heterogeneity. To accommodate this embodiment, the apparatus is designed to be essentially symmetrical about the core holder.

In a second embodiment pressure transient tests using small pressure transient vessels are run in a single direction on a core sample. Theoretical results which match the test results are then generated using numerical simulation. The coefficients obtained from the numerical simulation can be used to characterize and quantify a core fracture (transverse heterogeneity).

The two embodiments can also be practiced at the same time to characterize both heterogeneous matrix properties and fractures of the core.

In the most preferred embodiment of the apparatus, the apparatus has a plurality of vessels at each end of the core holder. The vessels should have a range of volumes. One vessel on each end should be a variable volume vessel with compressive storages small in comparison to the compressive storage of the core sample. The apparatus should be instrumented to collect pressures as a function of time. Direction of the test ("forward" or "reverse"), release of the pressure in the vessels to the core, and recording of the data can all be managed by a controlling computer.

OBJECTS OF THE INVENTION

It is therefore an object of the present invention to provide an improved method and apparatus for measuring multiple properties of a core sample using a single test apparatus.

Another object of the present invention is to provide an improvement method of measuring multiple rock properties using pressure transient techniques, and to provide apparatus for performing such method.

A further object of this invention is to provide a technique for rapid experimental determination of multiple rock properties of a core sample using pressure transient techniques and computer aided graphical display of experimental data.

Various other objects, advantages and features of the present invention will become readily apparent from the following detailed description.

BRIEF DESCRIPTION OF THE DRAWINGS

In order to facilitate the understanding of this invention, reference will now be made to the appended drawings of the preferred embodiments of the present invention.

DETAILED DESCRIPTION OF THE PREFERRED EMBODIMENTS

The invention described herein discloses a novel method for determining multiple properties of a core sample using a single test apparatus. The invention further discloses such a test apparatus.

In pressure transient testing of geologic core samples ("cores") the governing equation is:

$$\frac{K}{\mu L^2} \frac{\partial^2 P^*}{\partial \psi^2} = \phi C \frac{\partial P^*}{\partial t} \quad \text{(Equation 1)}$$

where

K is the permeability of the core;
$\mu$ is the fluid viscosity;
L is the length of the core;
P* is dimensionless pressure $$\frac{P(\psi,t) - P(\psi,0)}{P_u(0) - P_d(0)}$$

where $P_u$ and $P_d$ are upstream and downstream pressures, respectively, as functions of time t;
$\psi$ is dimensionless distance X/L where X is a distance along the core
$\phi$ is the fraction porosity of the core; and
C is the effective compressibility of the core.

Figure 1:
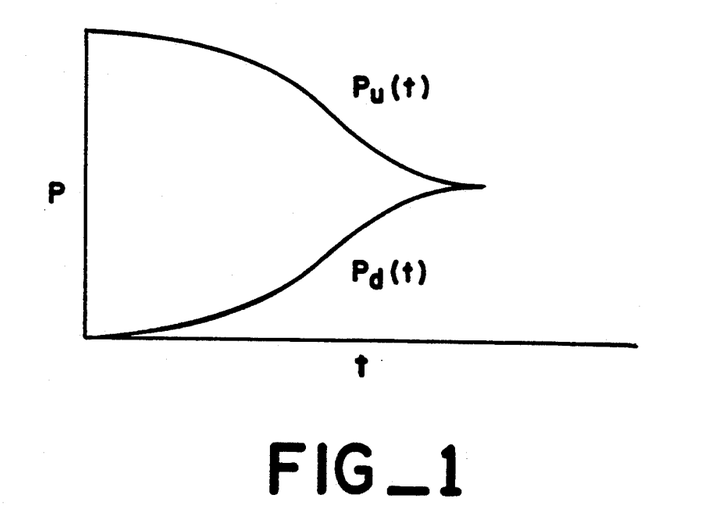
FIG. 1 is a graph showing the typical results of a pressure transient test known in the art.

By applying a pressure pulse to one end of the core and simultaneously measuring and plotting the pressure as a function of time at the upstream and downstream ends of the core, a plot similar to FIG. 1, a pressure transient plot, is obtained. With this plot, the permeability K can be obtained by calculation using Equation 1.

The invention makes use of the effect of compressive storage of the core during pressure transient testing. By compressive storage we mean the product of compressibility (typically that of the fluid) and volume (typically that of the fluid). The ratio of the core compressive storage with respect to the compressive storage of the upstream vessels is termed "$\beta$", and the ratio of the core compressive storage with respect to the downstream vessels is termed "$\beta^*$". Prior art recognized that when experimental designs use large compressive storage in the vessels (i.e., large $\beta$ and/or $\beta^*$), the permeability can be calculated directly and simply. In addition, the use of large compressive storage in vessels lead to longer test times, which were often designed for ease of pressure data gathering. Thus, prior art has taught away from the use of pressure transient configurations where small compressive storage vessels are used. We have discovered that configurations having small compressive storage vessels can provide information about the heterogeneities of the core which cannot be obtained when large compressive storage vessels are used. Specifically, when small compressive storage vessels are used, deviations from homogeneous core responses can be analyzed to quantify heterogeneities. More specifically, large vessels are first selected to obtain effective (i.e., overall or bulk) properties of heterogeneous cores (e.g., fractured cores), using standard analytical solutions of homogeneous cores. Smaller vessels are then used to accentuate differences between the homogeneous and heterogeneous core responses. These differences are then analyzed to quantify the heterogeneities, e.g., variation in core matrix properties and core fracture properties. In this way fractures and discontinuities which lie in a plane parallel to the cylindrical axis of the core, i.e., longitudinal heterogeneities, as well as graduations in permeability which vary as a function of a distance X along a core, can be discerned. By "core matrix properties" we mean the properties particular to the structure of the core or rock, such as grain size, permeability, porosity, etc.

P. A. Hsieh, et al., have determined the theoretical solution to the pressure-time decay problem ("A Transient Laboratory Method for Determining the Hydraulic Properties of Tight Rocks - I. Theory," Int. J. Rock Mech. Min. Sci. and Geomech. Abstr. (1981), Vol. 18, p. 245-252) as being:

$$P^*(\psi,t) = \frac{1}{1+\beta+\gamma} + 2 \sum_{m=1}^{\infty} \frac{\exp(-\alpha\phi_m^2)\left[\cos\phi_m\psi - \left(\frac{\gamma_m}{\beta}\right)\sin\phi_m\psi\right]}{\left(1+\beta+\gamma-\frac{\gamma\phi^2}{\beta}\right)\cos\phi_m - \phi_m\left(1+\gamma+\frac{2\gamma}{\beta}\right)\sin\phi_m} \quad \text{(Equation 2)}$$

where
$\phi$ is the porosity of the core (fraction);
$\phi_m$ are the roots of $$\tan\phi = ((\gamma+1)\phi)/((\gamma\phi^2/\beta) - \beta);$$
$$\alpha = \frac{Kt}{\mu\phi CL^2}, \quad \beta = \frac{A\phi CL}{C_u V_u}, \quad \gamma = \frac{C_d V_d}{C_u V_u}$$

C is compressibility, V is volume and subscription u and d refer respectively to upstream and downstream values thereof; and A is the cross sectional area of the core. Equation 2 has early time solution $$\sqrt{t}\,\frac{dP_u^*}{dt} = \lambda(P_u^*\sqrt{t}) - \sqrt{\frac{\lambda}{\pi}} \quad \text{(Equation 3)}$$

where $$\lambda = \frac{KA^2\phi C}{\mu(C_u V_u)^2}$$

and Equation 2 has late time solution $$-\frac{1}{\phi_1^2\left(P_u^* - \frac{1}{1+\gamma+\beta}\right)}\left(\frac{dP_u^*}{dt}\right) = \frac{K}{\mu\phi CL^2}. \quad \text{(Equation 4)}$$

Figure 2:
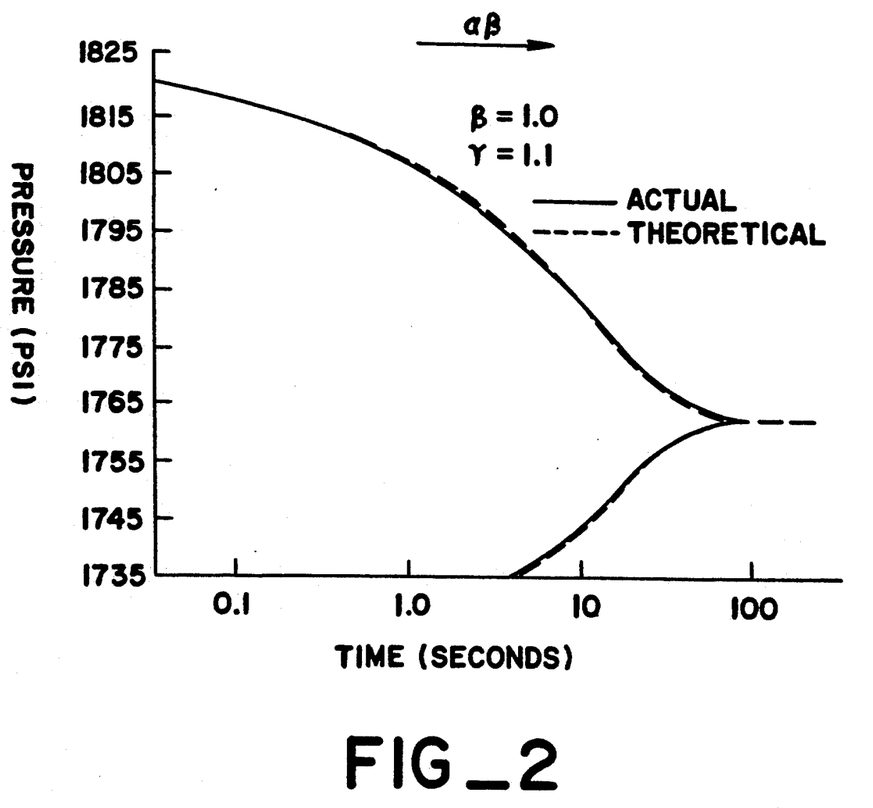
FIG. 2 is a graph comparing theoretical pressure transient test results to actual pressure transient test results.

By "early time solution" we mean the pressure-time behavior before the pressure disturbance has reached the downstream boundary. By "late time solution" we mean that portion of the solution which can be represented by a simple exponential, which occurs at the late stages of the pressure change. Equations 3 and 4 can be used to predict results for homogenous cores for difference comparison with heterogeneous cores, as will be described below. Equations 2, 3 and 4 are verified by FIG. 2 which shows a high correlation between the theoretical and actual pressure transient curves for a homogeneous sample.

The best mode will incorporate the following attributes:

High frequency of sampling of pressure as a function of time: the highest rate available for sampling should be employed, the present maximum being a rate of about 300 Hz, which is limited by poor noise rejection capabilities of the state of the art digital voltmeters. The rate should not be less that 50 Hz if possible. As the level of technology of digital voltmeters improves, higher sampling rates are desirable and may be achieved. The high rate of sampling is desirable due to the rapid rate of pressure decay when using small fluid vessels in the test configuration. Additionally, a rapid rate of sampling is desirable to record initial pressure drop in the "dead" volume of the lines leading from the core to the fluid reservoir. When small fluid reservoirs are used, such pressure drops can be significant and should be recorded for accurate interpretation of the data.

A test fluid with a low pressure change in response to temperature changes: this will minimize the effect that ambient temperature changes will have on test results. A fluid with a low value of $$\left(\frac{\partial P}{\partial T}\right)_v$$

should be chosen. Fluids such as water, toluene, and methanol with pressure/temperature sensitivities of approximately 1 MPa/°K are acceptable.

A test fluid which will have a minimum temperature change due to compression and expansion should be selected: this will minimize pressure changes, as described in the previous paragraph. A fluid with a low value of $$\frac{T}{C_p}\left(\frac{\partial v}{\partial T}\right)_p$$

should be chosen. Water, with a value of 0.01 K/MPa, is most preferable. However, as oil permeability is often the desired quantity, the experimental setup should be designed such that the pressure transient vessels contain water and the core can be saturated with any desired fluid, such as oil.

A range of upstream and downstream vessel sizes should be incorporated into the testing apparatus: this is necessary to collect sufficient data highlighting the difference in response between a homogeneous core and a heterogeneous core to allow analysis of the differences. The arrangement of vessels and connections at each end of the core testing apparatus should be as nearly identical as possible. Each arrangement of vessels should be capable of generating $\beta$'s ranging from 0.001 to 10.0. Preferably, each arrangement contains a variable volume vessel such that a range of $\beta$'s, e.g., from 1 to 10, can be achieved with this vessel alone. In such a case two other vessels at each end of the apparatus with $\beta$'s of 0.1 and 0.001 would then be used along with the variable volume vessel.

Account should be taken of the volumes in the lines between the vessels and the cores when $\beta$'s are large. The lines should be designed so as to minimize their volume, which will have the effect of decreasing $\beta$, an undesirable effect when large $\beta$'s are sought. However, the lines should not be designed with such a small volume that flow out of and into the vessels is restricted. Pressure transducers should be placed as near the ends of the core as possible. Additionally, a second set of transducers should be placed as near the inlet/outlet of the vessels as possible. In this way, the effect the leads have on the results of the experiment can be monitored.

The test apparatus should be designed symmetrically: as discussed above, with respect to the vessels, connecting lines, connectors and instrumentation, the core testing apparatus should be symmetrical about the core holder. This is important since tests are preferably run in both the forward and reverse directions, and the two results compared to detect and characterize heterogeneities. Differences in geometry of the two halves of the test apparatus can lead to differences in data not due to heterogeneities, and thus can be misleading.

Pulse size should be limited to approximately 10% of the effective pressure: the size of the pulse should be guided by a percentage of the effective pressure (i.e., the overburden pressure minus the pore pressure), rather than as a percentage of the pore pressure, as was done in prior art.

Pressure measuring system to optimize accuracy, repeatability, resolution, and quick response time: Accuracy in the context of a pulse decay test refers to ability to measure changes from an initial state, and not to absolute accuracy; i.e., change in pressure is the desired quantity. It appears that with current technology, accuracy and repeatability are functions of resolution and sampling rate. As discussed earlier, a high sampling rate is desired. However, as sampling rate increases, resolution, and thus accuracy and repeatability decrease. A system having a sampling rate of 333 Hz and a resolution of 1 psi (7 kPa) or a system with a sampling rate of 10 Hz and a resolution of 0.1 psi (0.7 kPa) can be used. The selection will depend primarily on the permeability of the core, the size of the smallest vessel used, and the initial differential pressure between the upstream and downstream ends of the core. That is, where rapid pressure decays are anticipated, a high rate of sampling is preferable over resolution. Alternately, two systems could be employed, a high speed, low resolution system for measuring pressure decay when $\beta$'s are large, and a lower speed, higher resolution system for measuring pressure decay when $\beta$'s are small.

Figure 3:
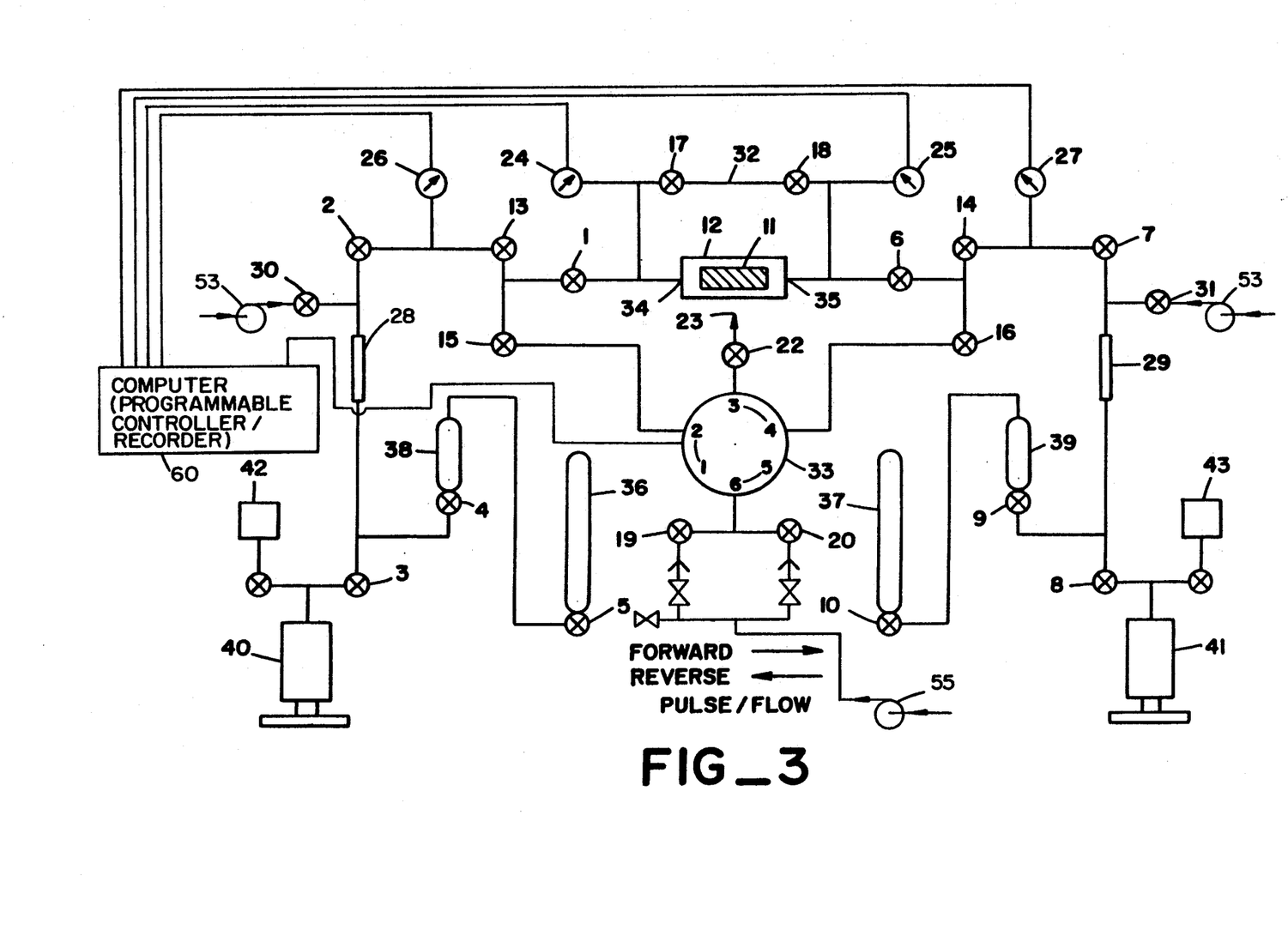
FIG. 3 is a schematic drawing showing one embodiment of the claimed apparatus.

All of the examples described below incorporated the preferred embodiments of the invention as described above. The data from each example was processed by a commercially available computer graphical data analysis package well known in the art. The same core testing apparatus was used for all examples. The apparatus used is shown in FIG. 3.

The Apparatus: Referring now to FIG. 3 which shows the pressure transient apparatus, a work piece core 11 is constrained within a core holder 12, shown in cross section. Core holders are known in the art and are known by such names as "Hassler Cells". The core holder is air-tight except for holder connections 34 and 35 at a first and second end, respectively. Holder connections 34 and 35 are also connected to bypass valves 17 and 18, which allow flow to be diverted around the core holder through the bypass line 32. The components connected to connections 34 and 35 at each end of the core holder are preferentially nearly identical, and for purposes of description the components 4 will not be referred to as "component 'X' at the first end and component 'Y' at the second end", but merely identical "components 'X' and 'Y'". Alternately, the ends may be referred to as "upstream" and "downstream", however, this designation is not meant to limit flow to only flow in the downstream direction. When the detailed operation of the components is discussed, reference will be to components by end.

Connected to each end of the core holder are the pressure transient storage vessels ("vessels") and tubing assemblies having various components for isolation of the vessels and measurement of the pressure decay and the like. Specifically, primary pressure transducers 24 and 25 are connected as close to the core holder ends as possible. Secondary pressure transducers 26 and 27 are located near the inlet/outlet connections to the pressure transient storage vessels. Between the primary and secondary transducers are located manual isolation valves ("isolation valves") 1 and 6. Between isolation valves 1 and 6 and the secondary transducers 26 and 27 are located the high speed computer controlled pulse valves 13 and 14 and flow control valves 15 and 16. The flow control valves 15 and 16 keep the flow direction valve 33 and its associated apparatus isolated from the pressure transient apparatus during pressure transient tests. The flow direction valve 33 can be automatically operated and is used to reverse the flow during experiments, as described below. The terms "flow direction valve" and "reverse flow valve" can be used interchangeably. Thus, valve 33 could be an automatically operated reverse flow valve operated by computer 60. The computer which is referred to which controls the sequencing of the valves and the recording of data is shown in FIG. 3 as item 60. Such computers and their use as described herein are well known in the art.

Between the secondary transducers 26 and 27 and the pressure transient storage vessels 36, 37, 38, 39, 40, and 41 are located the isolation vessels 28 and 29. Isolation vessel 28 is disposed between first valve means 2 and 7, and second valve means 3; isolation vessel 29 is disposed between first valve means 7 and second valve means 8. Valves 2, 3, 7, and 8 are shown in FIG. 3 and are described below. The isolation vessels perform the function of separating two different test fluids if a first fluid is used in the vessels and a second fluid is used to saturate the core. For example, the fluid in the vessels might be chosen to be water because of its desirable properties as a pressure transient fluid, as discussed above, while the fluid in the core might be a different fluid, such as oil, for which the core permeability is desired to be known for. The vessels in this example consist of two nearly identical sets of three vessels each. The large vessels 36 and 37 are sized to have $\beta$ values of between 0.001 and 0.01. The actual size of the vessel will depend on the anticipated compressive storage of the core, but a vessel of approximately 4,000 cc should cover most anticipated tests. The two mid-range vessels 38 and 39 with $\beta$ values of between 0.01 and 0.2 have volumes of approximately 300 to 500 cc. The small vessels 40 and 41 should have large $\beta$ values in the range of 1 to 10. Since data should be collected for large values of $\beta$ (i.e, about $\beta = 1$), and since $\beta$ values are particularly sensitive to core compressive storage, variable volume vessels are preferable for the two smallest vessels. By variable volume we mean a volume that can be increased or decreased to a known volume using the same vessel. The selection criteria for the small volume vessels is to select a volume sufficiently small that a measurable variance from the theoretical response curve to the actual pressure transient response curve occurs. In the example, the variable volume vessels have volumes variable from 4 cc to 30 cc. These are commercially available hand screw operated piston pumps known as "high pressure generators". Vessels can also be fitted with instrumentation as desired, such as thermocouples.

Each of the three vessels in each set is isolated from the other vessels by isolation valves: large vessel isolation valves 5 and 10, mid-range vessel isolation valves 4 and 9, and variable volume vessel isolation valves 4 and 9, and example, valves 3 and 8 were two stem three way valves with connection to reservoirs 42 and 43. The reservoirs provide a source and a storage location for fluid used in the apparatus. In the example apparatus just described, only three vessels at each end of the core were used. However, more vessels could be used. Alternately, an apparatus with less than three vessels could be used, especially where the vessels are variable volume vessels. A single large vessel at each end of the core could be used and the volume varied by adding or removing mercury with for example a positive displacement metering pump. In the remaining detailed description, "the apparatus" will mean the apparatus of FIG. 3 just as described in detail.

The essential components of the apparatus are the core holder 12, the pulse valves 13 and 14, the controlling computer 60, the primary and secondary pressure transducers 24, 25, 26, and 27, the pressure transient vessels 36, 37, 38, 39, 40, and 41 and the vessel isolation valves 3, 4, 5, 8, 9 and 10. The other components described above provide additional features which enhance operation of the apparatus.

Operation of the Apparatus: The apparatus should be initially charged with fluid to purge any non-test fluids and, if a liquid is used, to insure that no vapor is present in the apparatus. The steady state as well as the effective permeability of a heterogeneous core can be determined with the apparatus of FIG. 3. With reference to FIG. 3, this is accomplished by placing the core 11 in core holder 12, and isolating the core from the pressure transient vessels by isolation valves 2 and 7. With valves 1, 6, 15 and 16 open a fluid is pumped through valve 19 or 20, discharging the liquid through valve 22, measuring the rate of liquid flow, measuring the pressure difference across the core using transducers 26 and 27, or 24 and 25, and calculating the permeability by means known in the art. A back-pressure regulator can also be connected to the outlet of valve 22 at 23 in order to maintain a minimum core pressure. Flow direction valve 33 can be used to reverse the flow of fluid through the core to get both "forward" and "reverse" flow permeabilities.

Pressure Transient Testing Using Apparatus: If two different fluids are used, i.e., a core saturating fluid in the core and a pressure transient fluid in the vessels, the isolation vessels 28 and 29 should be used as the interface between the two fluids. The fluid interface in the isolation vessels should be near the mid-level point of the vessel. If two fluids are used, the purging described in the above section can be done in two steps using the vent valves 30 and 31 to insure that mixing of the two fluids in the pressure transient vessels or the core does not occur. Between experiments, the pressure transient vessels can be isolated from the core by cut-off valves 1 and 6 so that only the core will have to be purged, rather than the whole apparatus. The compressibility or compressive storage of the pressure transient vessels and their associated connections can be determined by closing the pulse valves 13 and 14, decreasing the volume of the variable volume vessels 40 and 41 by a predetermined amount, measuring the pressure rise in the system with the transducers 26 and 27, and calculating the compressive storage by dividing the volume change by the pressure rise.

The general method for pressure transient testing is essentially the same in all cases, i.e., one end of the apparatus, which will be called the "upstream" end, is isolated from the core and the other end of the apparatus, which will be called the "downstream" end, by one of the high speed computer controlled pulse valves 13 or 14. The Closed pulse valve will be on the upstream end. The pressure in the upstream end is increased approximately 10% above the effective pressure of the fluid in the core. The pressure can be increased by any common means such as by connecting a pump to valve 30 or 31, or by compressing the fluid in the upstream end by reducing the volume of the upstream variable volume vessel. Additionally, a single pressure increasing means could be employed by connecting a pump, for example 55, to an external port of the flow direction valve 33. The flow direction valve would then be used to direct the pump output to either the upstream end of the downstream end of the apparatus, while isolating it from the other respective end. The computer controlled data acquisition is then started which will collect pressure data from transducers 24, 25, 26 and 27 for approximately five seconds to establish a baseline of background noise. Once the baseline has been established the computer controller opens the upstream pulse valve to allow the pressure in the upstream end to decay into the core and the downstream end. Pressure data is recorded as a function of time at each transducer while this pressure decay is occurring and recording continues until equilibrium between the upstream and downstream ends is essentially achieved. At this time the bypass line 32 can be used to insure that complete equilibrium is reached. The bypass can also be kept open while the system pressure is restored to the initial or effective pressure. The process of increasing the pressure in the upstream end, releasing the pressure into the core and downstream end, and recording the pressure-time data throughout the pressure decay period can be repeated with various combinations of upstream and downstream vessels and with reverse direction to allow a sufficient amount of data to be collected for purposes of analysis. Typically, three or four pressure transient tests in each direction would be run with ever decreasing vessel volumes (i.e., increasing $\beta$'s). The timepressure relationship can also be measured at a point along the length of the core by the addition of a pressure transducer 50 as shown in FIG. 3. This will allow additional data to be collected.

Figures 4A, 4B, 5:
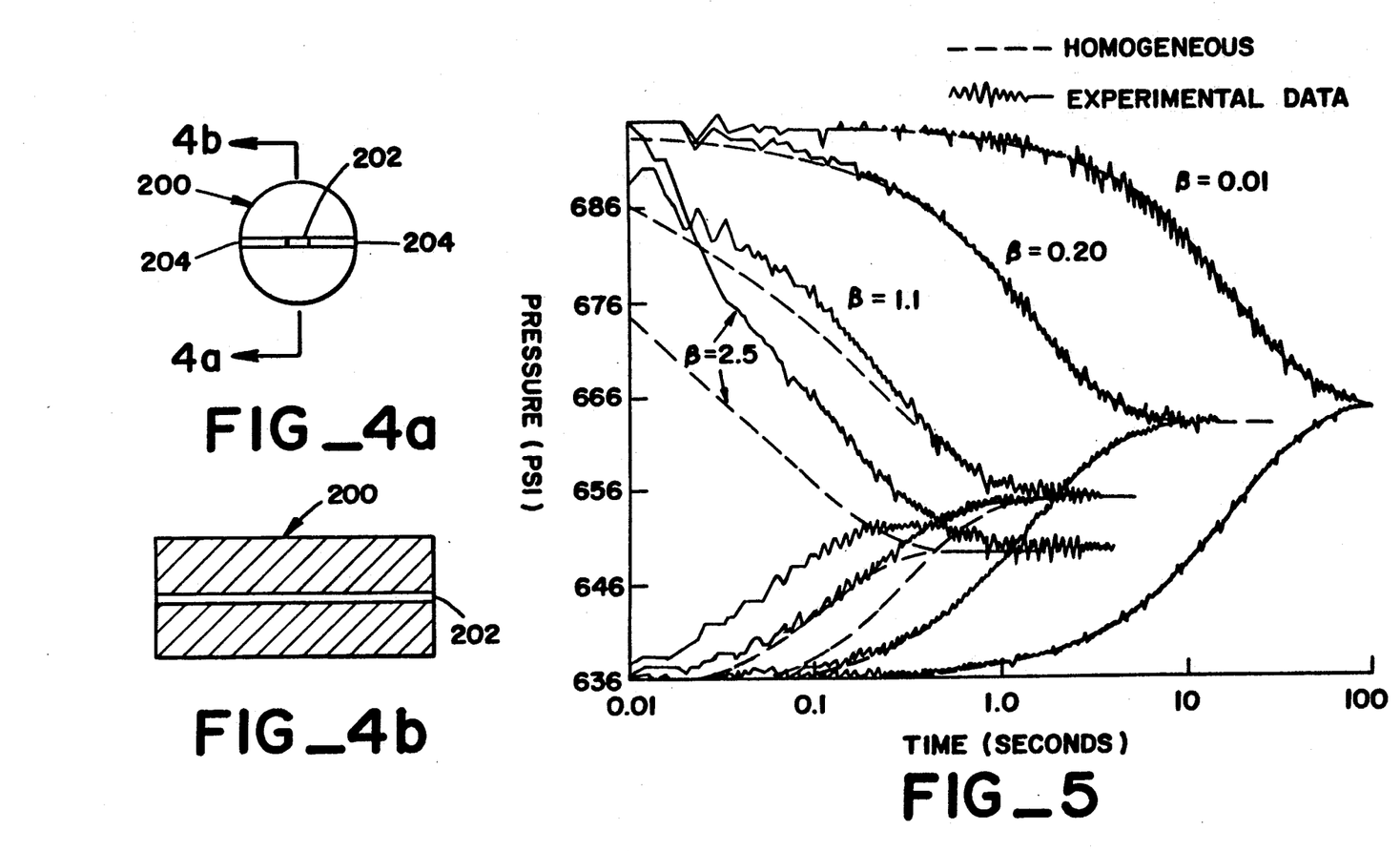
FIG. 4a and FIG. 4b are respectively a cross sectional end view and a cross sectional elevation view of a rock core having a synthetic transverse heterogeneity.
FIG. 5 is a graph showing the results of a pressure transient test on the core of FIGS. 4a and 4b using the claimed method and apparatus and comparing the test results with the analytical solution.
Figure 6:
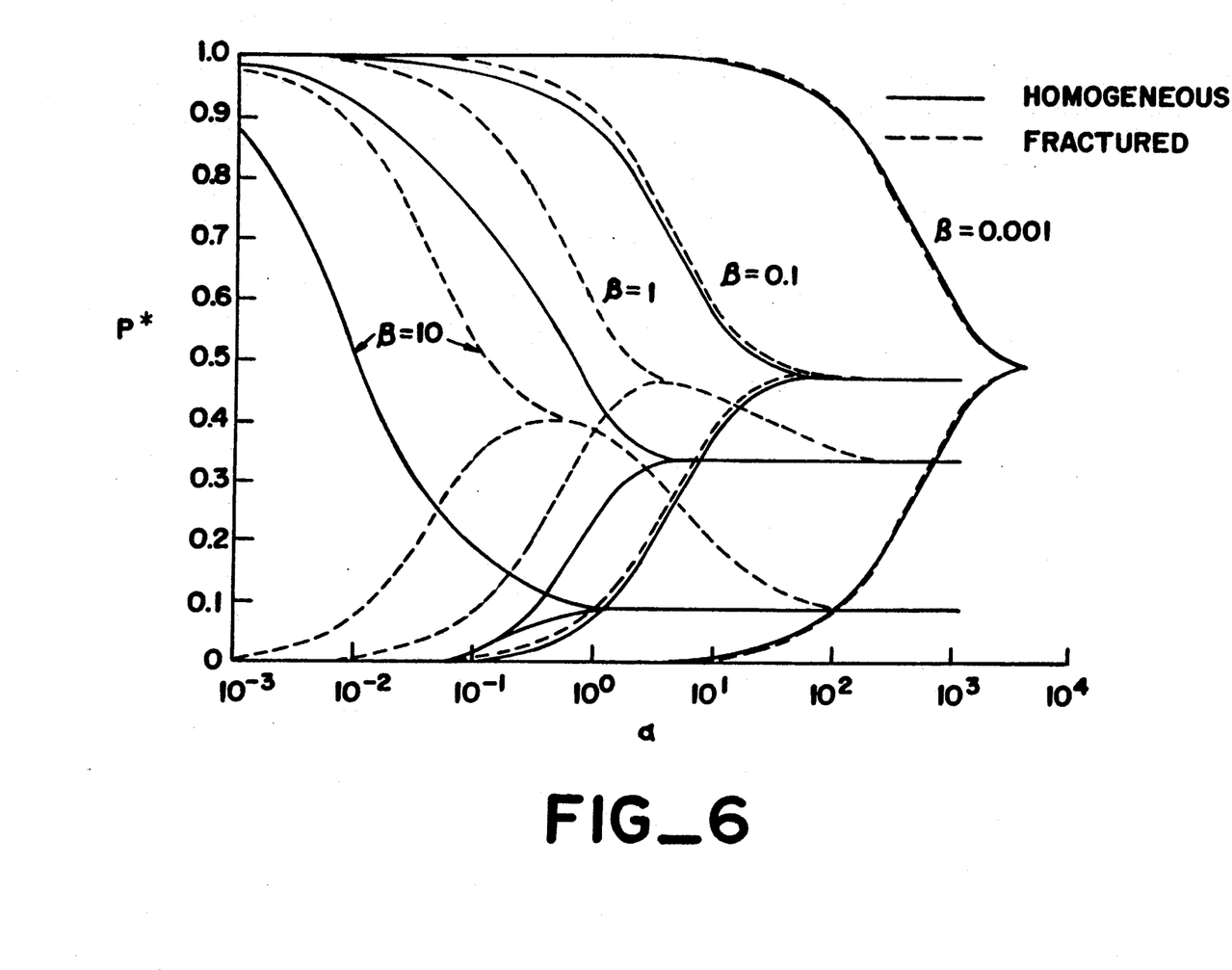
FIG. 6 is a graph comparing the theoretical pressure transient response of a fractured core and a homogeneous core.

Pressure Transient Test Results: To check the accuracy of the method of determining core heterogeneities using pressure transients, cores having known synthetic heterogeneities were tested using the method described below. The results using the method were then reviewed to see how accurately they predicted the known heterogeneities. The two heterogeneities modelled were (i) a transverse heterogeneity (here, a longitudinal fracture); and (ii) a longitudinal heterogeneity (here, an abrupt permeability change along the axis). By "transverse heterogeneity" we mean a discontinuity in a plane of the core transverse to the lengthwise axis of the core. By "longitudinal heterogeneity" we mean a discontinuity in a plane of the core parallel to the lengthwise axis of the core. In the example wherein the core has a transverse heterogeneity, as shown in FIGS. 4a and 4b, a sample of Colton sandstone 200 was split and a channel 202 0.2 cm by 20 m was formed using aluminum shims 204. The steady state permeability was first established as described above. Pressure transients were then performed using the method described above. $\beta$ values of 0.01, 0.20, 1.1, and 2.5 were used. Theoretical analytical results were then obtained using Equations 3 and 4 for the above values of $\beta$. The results from the pressure transient testing were then graphically compared with the results from the analytical solution and are shown in FIG. 5. The deviation of the data from the analytical solution becomes more pronounced as $\beta$ becomes larger. FIG. 6 is a graph of theoretical pressure responses from two different cores having the same effective permeability. One set of curves in FIG. 6 is for a homogeneous core, the second set of curves is for a heterogeneous (fractured) core. When FIG. 5 is compared with FIG. 6, the similarity between the pressure responses for the fractured cores is clearly visible. Thus, when a set of pressure transient curves exhibiting a signature similar to those of FIG. 5 is obtained, one will suspect that a fracture in the core is present, and will be on notice that the permeability is partially due to the fracture, and not just the matrix itself.

Matrix and fracture properties can be quantified by first defining the following two parameters:

$$\lambda = (K_m K_f) S$$

and $$\omega = (C_f V_f)/((C_f V_f) + (C_m V_m))$$

where
K = permeability;
S = shape factor, a function of geometry;
V = volume;
f = fracture;
m = matrix; and
C = compressibility.

Figures 7, 8:
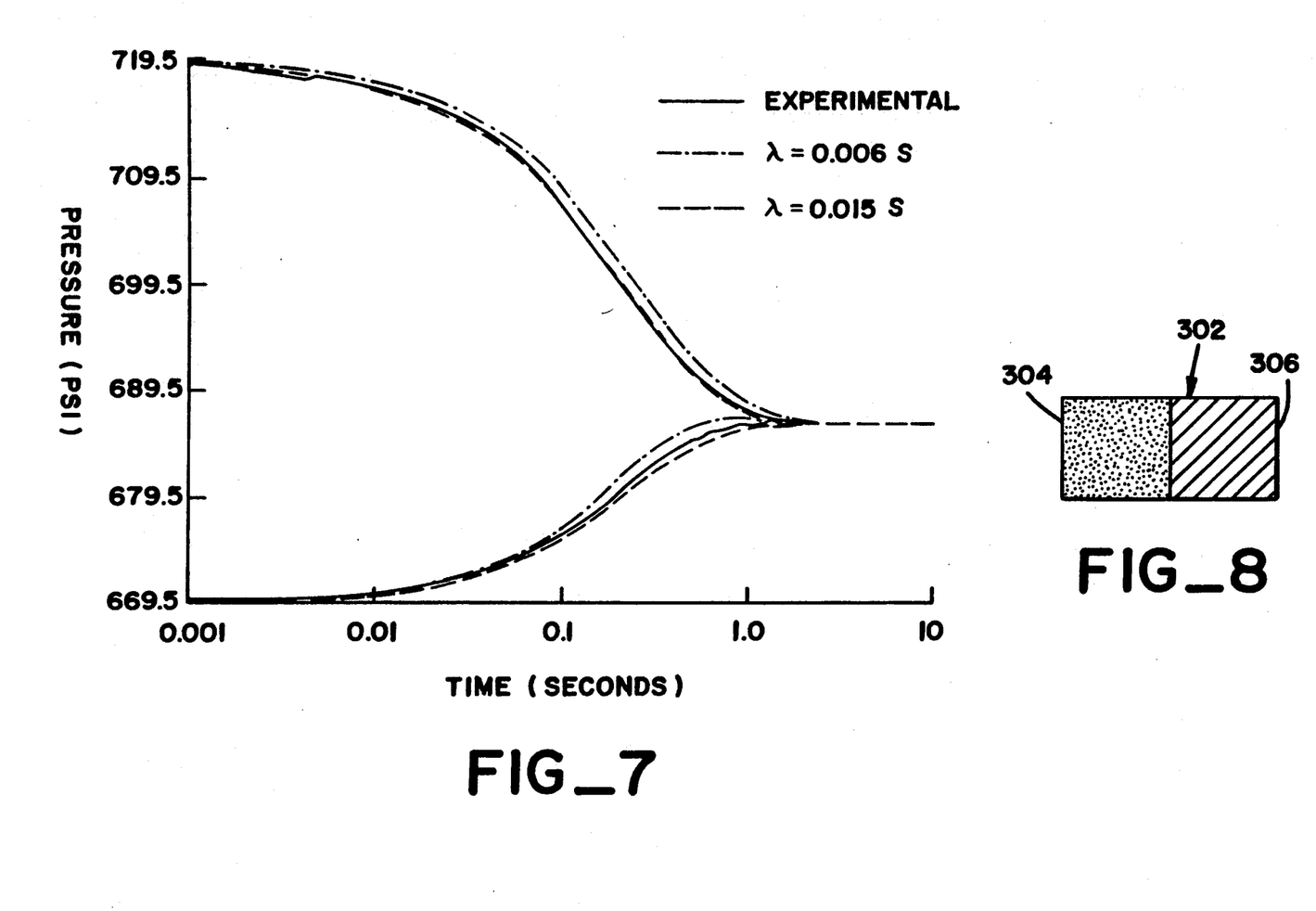
FIG. 7 is a graph comparing experimental results of a pressure transient test on a fractured sandstone to numerically calculated results.
FIG. 8 is a longitudinal cross sectional drawing of a rock core having a synthetic longitudinal heterogeneity.

Theoretical solutions for different values of $\lambda$ and $\omega$ are then used to match the experimental data as shown in FIG. 7. The match values of $\lambda$ and $\omega$ can then be used to calculate fracture and matrix properties.

Figure 9:
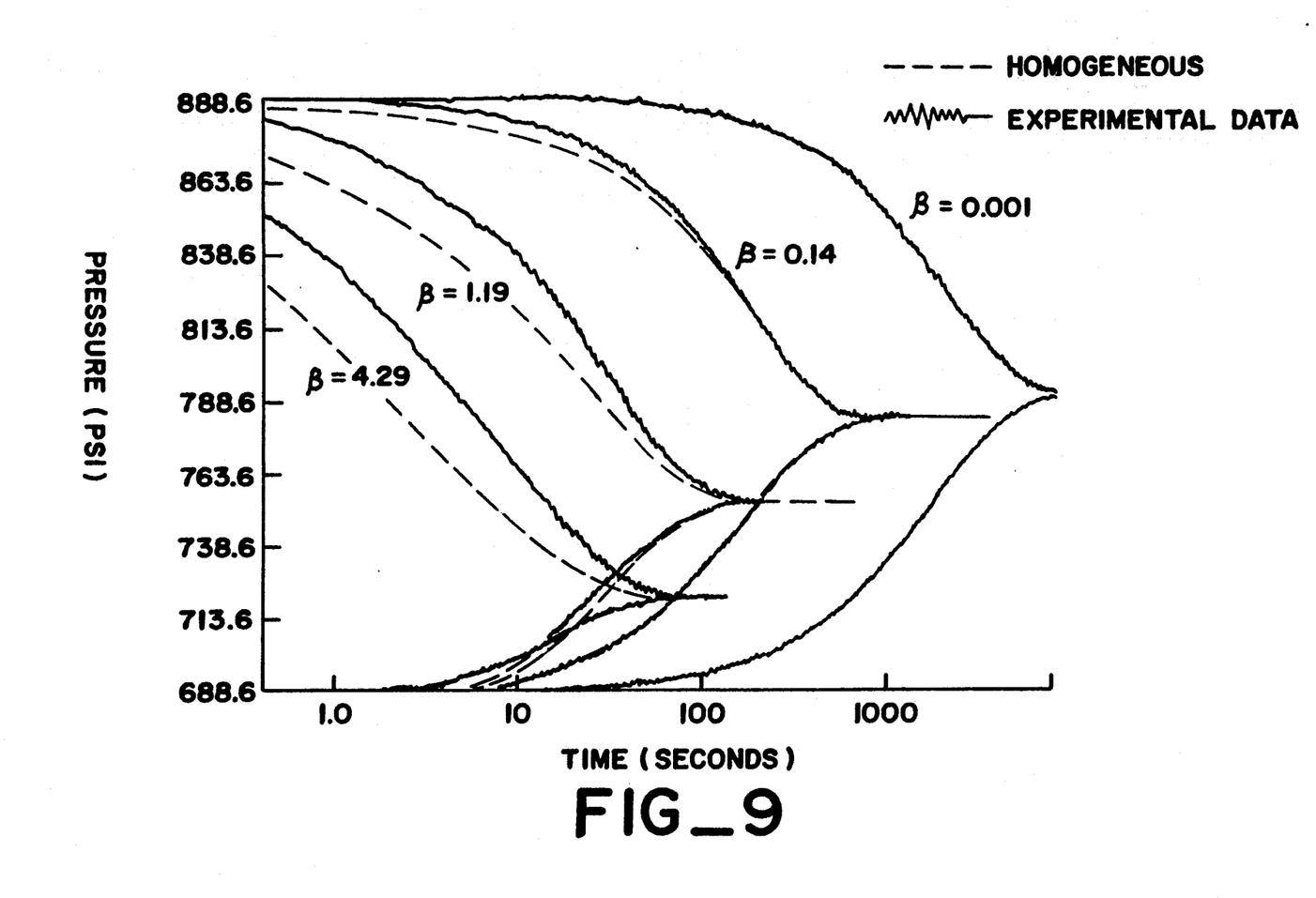
FIG. 9 is a graph of the results of a pressure transient test in the "forward" direction on the rock core of FIG. 8.
Figure 10:
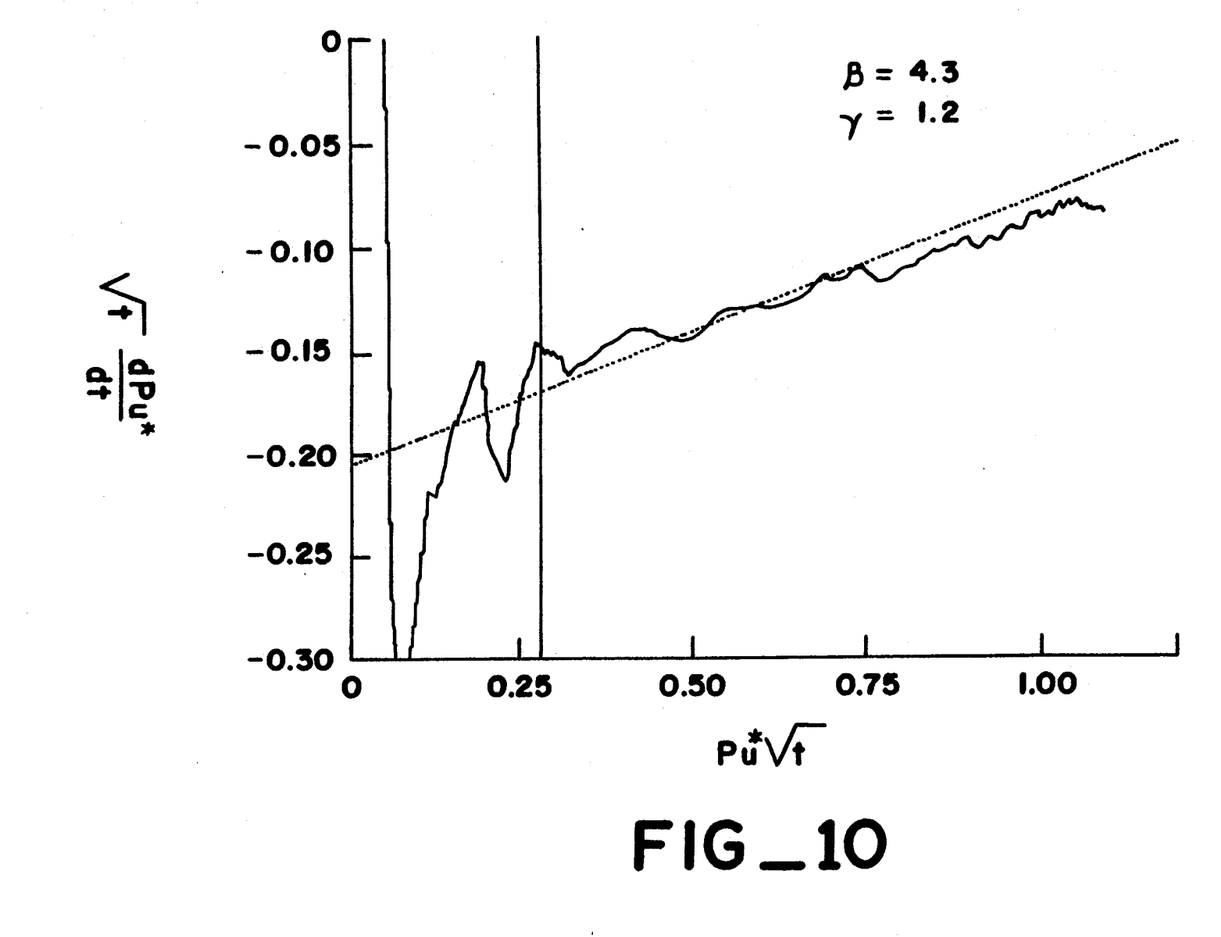
FIG. 10 is a graph of the results of the test of FIG. 9 for $\beta = 4.3$, plotted as a function of derivative pressure.

Referring now to FIG. 8, a core 302 with longitudinal heterogeneity was synthetically fabricated by butting a core of Colton sandstone 304 against a core of Torrey sandstone 306. The effective permeability was first obtained using the method described above for the transverse heterogeneity test. Theoretical results were then obtained for a core having the effective permeability as measured. Pressure transient tests were then run for $\beta$'s of 0.001, 0.14, 1.2, and 4.3 for pulses in the "forward" direction (i.e., from the Colton to the Torrey sandstone). The results are shown graphically in FIG. 9. The increasing discrepancy between the theoretical solution and the experimental responses as the value of $\beta$ increases is indicative of the presence of a heterogeneity in the core sample. The results for $\beta = 4.3$ are also shown graphically in FIG. 10 where the derivative group.

$$\sqrt{t} \, \frac{dP_u^*}{dt} \text{ is plotted against the pressure group } P_u^* \sqrt{t}.$$

Figure 11:
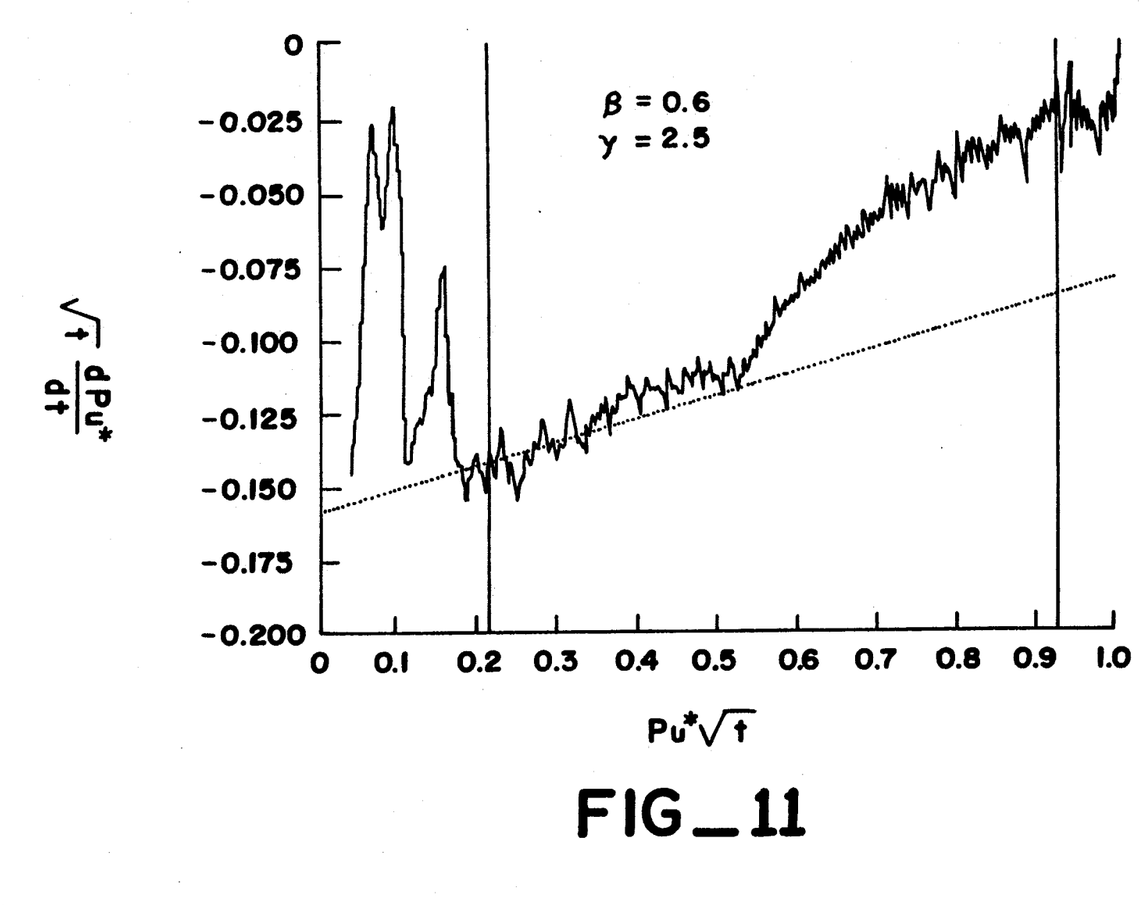
FIG. 11 is a graph of the results for $\beta = 0.6$ of a pressure transient test performed in the "reverse" direction on the rock core of FIG. 8, plotted as a function of derivative pressure.

Using Equation 3 and fitting a straight line to that part of the data of FIG. 10 which is closest to the time origin, the permeability of the region closest to the pulsing end can be calculated. In so doing, the first few points closest to $t=0$ may need to be ignored, since they are more subject to noise effects. This straight line is constrained in that it has related slope and intercept, and hence the calculated value of permeability is usually unique to the pulsing end. The pressure transient experiment is then run in the opposite (37 reverse") direction and the same derivative groups are plotted, as shown in FIG. 11. By using the same above analysis, the permeability of the region closest to that pulsing end ("reverse end") is calculated. In this manner the two different permeabilities of the core sample can be determined.

The location of the interface of the two regions of different permeability may be calculated by noting the time at which there is deviation from linearity in the $$\sqrt{t} \, \frac{dP_u^*}{dt} \text{ versus } P_u^* \sqrt{t} \text{ plot.}$$

Then the position of the interface, "i", can be calculated from $$I = \sqrt{\frac{5kt}{\mu \phi C}}, \text{ where}$$

k = permeability of the core closest to the pulsing end,
t = time at which deviation from linearity occurs,
$\phi$ = porosity,
C = compressibility, and
$\mu$ = viscosity.

The above method for determining an interface of a permeability discontinuity can also be used to determine the presence of a fluid front (i.e., the juncture of two distinct fluids) within a core, since permeability is fluid dependent.

From the above description it is evident that the present invention provides an apparatus and method for determining various properties of a geologic core by use of pressure transients and variable reservoir volumes. Although only specific embodiments of the present invention have been described in detail, the invention is not limited thereto but is meant to include all embodiments coming within the scope of the appended claims.

What is claimed is:

1. A method of determining properties of a core sample, comprising the steps of:
   (a) applying a predetermined upstream pressure to a first closed vessel in fluid communication with the upstream end of a core sample, said upstream pressure being greater than a predetermined system pressure existing in said core sample and the downstream pressure of a second closed vessel to which the downstream end of said core sample exits, one of said closed vessels having a $\beta$ ratio sufficiently high to cause a measurable variance between an actual pressure transient response for the system and a theoretical pressure transient response for said system;
   (b) allowing said upstream pressure to dissipate into said downstream end of said core sample;
   (c) measuring the pressure at a preselected end of said core sample at predetermined time intervals during said dissipation of said upstream pressure; and
   (d) analyzing said variance to detect non-homogenous rock properties of said core sample.

2. The method of claim 1, further comprising the step of measuring the pressure at a point along the length of said core at predetermined time intervals during said dissipation of said upstream pressure.

3. The method of claim 1 further comprising the step of measuring the pressure at the end of said core opposite said preselected end at predetermined time intervals during said dissipation of said upstream pressure.

4. A method of determining properties of a core sample, comprising the steps of:
   (a) applying a first predetermined pressure to a first closed vessel in fluid communication with the upstream end of a core sample in a test system, said first pressure being greater than a predetermined system pressure existing in said core sample and the pressure of a second closed vessel in fluid communication with the downstream end of said core sample;
   (b) allowing said first pressure to dissipate into said downstream end of said core sample;
   (c) measuring the pressure at a preselected end of said core sample at predetermined time intervals during said dissipation of said first pressure;
   (d) varying the volume of at least one of said closed vessels such that said vessel having a varied volume has a $\beta$ ratio sufficiently high to cause a measurable variance between an actual pressure transient response for the system and a theoretical pressure transient response for said system;
   (e) applying a second predetermined pressure to said first closed vessel, said second pressure being greater than a predetermined system pressure existing in said core sample and said downstream pressure;
   (f) allowing said second pressure to dissipate into said downstream end of said core sample;
   (g) measuring the pressure at said preselected end of said core sample at predetermined time intervals during said dissipation of said second pressure;
   (h) analyzing measurements made in steps (c) and (g) and the variance of step (d) to detect non-homogeneous rock properties of said core sample.

5. The method of claim 4 wherein at least one of said closed vessels is a variable volume vessel and said second pressure is generated by constricting the volume of said variable volume vessel.

6. The method of claim 5 further comprising the steps of:
   (a) following step (c), measuring the pressure at a point along the length of said core at predetermined time intervals during said dissipation of said first pressure; and
   (b) following step (g), measuring the pressure at a point along the length of said core at predetermined time intervals during said dissipation of said second pressure.

7. The method of claim 5 further comprising the steps of:
   (a) following step (c), measuring the pressure at the end of said core opposite said preselected end at predetermined time intervals during said dissipation of said first pressure; and
   (b) following step (g) of claim 1, measuring the pressure at the end of said core opposite said preselected end at predetermined time intervals during said dissipation of said second pressure.

8. The method of claim 7 further comprising steps of plotting said measurements of upstream and downstream pressures as a function of time and said step of detecting non-homogeneous rock properties of said core sample is accomplished using graphical techniques.

9. The method of claim 8 further comprising the step of generating numerical solution to $$\lambda = (K_m/K_f)S \text{ and } \omega = (C_f V_f)/((C_f V_f) + (C_m V_m))$$

such that said solutions essentially replicate said plotted measurements and values of $K_m$, $K_f$, $C_f$, $V_f$, $C_m$, and $V_m$ are determined for said core sample.

10. The method of claim 8 wherein said variance is analyzed to detect a fluid from within said core sample.

11. The method of claim 8 wherein said non-homogeneous rock property is a longitudinal heterogeneity.

12. The method of claim 8 wherein:
   (a) said predetermined pressures are applied when each of said vessels have a $\beta$ ratio sufficiently high to cause a measurable variance between an actual pressure transient response for the system and a theoretical pressure transient response for said system; and
   (b) said variance is analyzed to detect non-homogeneous rock properties of said core sample.

13. The method of claim 12 wherein said non-homogeneous rock property is a transverse heterogeneity.

14. A method of determining properties of a core sample, comprising the steps of:
   in a system for holding a core sample, said system having a first and a second end at the respective ends of said core sample, and having at least one closed vessel at each end in fluid communication with said core sample, and wherein at least one of said closed vessels has a $\beta$ ratio sufficiently high to cause a measurable variance between an actual pressure transient response and a theoretical pressure transient response for said system,
   (a) applying a first predetermined pressure to a first closed vessel at said first end of said core sample, said first predetermined pressure being greater than a predetermined system pressure existing in said core sample and the pressure at a second closed vessel at said second end of said core sample;
   (b) allowing said first predetermined pressure to dissipate into said second closed vessel;
   (c) measuring the pressure at a preselected end of said core sample at predetermined time intervals during said dissipation of said first predetermined pressure;
   (d) applying a second predetermined pressure at said second end of said core sample, said second predetermined pressure being greater than a predetermined system pressure existing in said core sample and the pressure at said first closed vessel;
   (e) allowing said second predetermined pressure to dissipate into said first closed vessel;
   (f) measuring the pressure at a preselected end of said core sample at predetermined time intervals during said dissipation of said second predetermined pressure; and
   (g) analyzing measurements made in steps (c) and (f), and said variance, to detect non-homogeneous rock properties of said core sample.

15. The method of claim 14 wherein said non-homogeneous rock property which is detected is a longitudinal heterogeneity.

16. The method of claim 15 wherein:
   (a) said longitudinal heterogeneity is with respect to permeability; and
   (b) said measurements are analyzed by comparing the solutions of $$\sqrt{t}\,\frac{dP_u{}^*}{dt} = \lambda(P_u{}^*\sqrt{t}) - \sqrt{\frac{\lambda}{\pi}}$$

for said first predetermined pressure dissipations and said second predetermined pressure dissipations.

17. Apparatus for use as a system in determining properties of a core sample, comprising:
  (a) sealed means for holding a core sample;
  (b) an upstream vessel in fluid communication with said core holding means such that fluid communication between said core and said upstream vessel may occur;
  (c) a downstream vessel in fluid communication with said core holding means such that fluid communication between said core and said downstream vessel may occur;
  (d) means for varying the volume of said upstream vessel such that said upstream vessel may have a $\beta$ ratio sufficiently high to cause a measurable variance between an actual pressure transient response for the system and a theoretical pressure transient response for said system;
  (e) upstream valve means for isolation said upstream vessel from said core holding means;
  (f) means for increasing the pressure in said upstream vessel above the pressure in said core holding means and said downstream vessel;
  (g) means for producing electrical signals corresponding to the pressure in at least one of said pressure vessels; and
  (h) means for recording said electrical signals at predetermined time intervals.

18. The apparatus as recited in claim 17, further comprising:
  (a) means for varying the volume of said downstream vessel such that said downstream vessel may have a $\beta$ ratio sufficiently high to cause a measurable variance between an actual pressure transient response for the system and a theoretical pressure transient response for said system;
  (b) downstream valve means for isolating said downstream vessel from said core holding means; and
  (c) means for increasing the pressure in said downstream vessel above the pressure in said core holding means and said upstream vessel.

19. The apparatus as recited in claim 18, further comprising:
  (a) a second upstream vessel of fixed volume in fluid communication with said core holding means such that fluid communication between said core and said second upstream vessel may occur, said second upstream vessel being of greater volume than said first upstream vessel;
  (b) second upstream valve means for isolating said second upstream vessel from said core holding means;
  (c) means for isolating said second upstream vessel from said first upstream vessel;
  (d) a second downstream vessel of fixed volume in fluid communication with said core holding means such that fluid communication between said core and said second downstream vessel may occur, said second downstream vessel being of greater volume than said first downstream vessel;
  (e) second downstream valve means for isolating said second downstream vessel from said core holding means;
  (f) means for isolating said second downstream vessel from said first downstream vessel;
  (g) means for increasing the pressure in said second downstream vessel above the pressure in said core holding means, and said upstream vessels; and
  (h) means for increasing the pressure in said second upstream vessel above the pressure in said core holding means and said downstream vessels.

20. The apparatus as recited in claim 19, further comprising:
  (a) a first isolation vessel, said first isolation vessel disposed between said first and second upstream valve means and said first and second upstream vessels; and
  (b) a second isolation vessel, said second isolation vessel disposed between said first and second downstream valve means and said first and second downstream vessels;
said isolation vessels each having a volume sufficient to maintain an interface between a first fluid saturating a core sample throughout a pressure transient test and a second fluid to be used in at least one of said upstream vessels and one of said downstream vessels during said pressure transient test.

21. The apparatus as recited in claim 20, wherein:
  (a) said first and said second upstream valve means are a single automatically operated upstream valve;
  (b) said first and said second downstream valve means are a single automatically operated downstream valve; and
  (c) said means for increasing the pressure in said second upstream vessel and said second downstream vessel is a single means being isolatable from each of said second upstream and said second downstream vessels by a single automatically operated reverse flow valve.

22. The apparatus as recited in claim 21 further comprising a controller means for:
  (a) operating said automatically operated downstream and upstream valves;
  (b) operating said automatically operated reverse flow valve; and
  (c) recording said electrical signals at said predetermined time intervals.

23. The apparatus as recited in claim 22 wherein said controller means is a programmable computer.

24. The apparatus as recited in claim 23 wherein $\beta$ ratios sufficiently high to cause a measurable variance between an actual pressure transient response for the system and a theoretical pressure transient response for said system are attainable by said first upstream and said first downstream variable volume vessels.

* * * * *